US006561010B2

(12) United States Patent
Wilson et al.

(10) Patent No.: US 6,561,010 B2
(45) Date of Patent: May 13, 2003

(54) APPARATUS AND METHOD FOR FLUID ANALYSIS

(75) Inventors: Bary W. Wilson, Richland, WA (US); Timothy J. Peters, Richland, WA (US); Chester L. Shepard, West Richland, WA (US); James H. Reeves, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/776,109

(22) Filed: Feb. 1, 2001

(65) Prior Publication Data

US 2001/0013247 A1 Aug. 16, 2001

Related U.S. Application Data

(63) Continuation-in-part of application No. 09/447,036, filed on Nov. 19, 1999.

(51) Int. Cl.[7] .................. G01N 11/00; G01N 21/25; G01M 3/20
(52) U.S. Cl. ................. 73/54.04; 73/36; 356/414
(58) Field of Search ............... 73/36, 54.01, 54.04, 73/54.07, 54.09, 54.23, 861.52; 250/343, 573; 356/414; 378/47; 702/108

(56) References Cited

U.S. PATENT DOCUMENTS

| 3,748,894 | A | * | 7/1973 | White et al. ............... 73/36 |
| 3,751,661 | A | * | 8/1973 | Packer et al. ............. 378/47 |
| 4,118,973 | A | * | 10/1978 | Tucker et al. ............ 73/54.07 |
| 4,125,769 | A | | 11/1978 | Marten et al. |
| 4,228,353 | A | | 10/1980 | Johnson |
| 4,277,971 | A | * | 7/1981 | Drzewiecki et al. ....... 73/54.09 |
| 4,388,530 | A | | 6/1983 | Lubecki et al. |
| 4,567,012 | A | | 1/1986 | Radcliff |
| 4,627,272 | A | * | 12/1986 | Wright .................... 73/54.23 |
| 4,649,711 | A | | 3/1987 | Sibley et al. |
| 4,683,759 | A | | 8/1987 | Skarsvaag et al. |
| 4,720,842 | A | | 1/1988 | Kira et al. |
| 4,721,874 | A | * | 1/1988 | Emmert ................... 310/333 |
| 4,750,351 | A | * | 6/1988 | Ball ........................ 73/54.04 |
| 4,795,903 | A | | 1/1989 | Clayton |
| 4,959,848 | A | | 9/1990 | Parobek |
| 4,959,995 | A | * | 10/1990 | Deysarkar et al. ........ 73/54.01 |
| 5,262,732 | A | * | 11/1993 | Dickert et al. ............ 324/672 |
| 5,377,531 | A | | 1/1995 | Gomm |
| 5,422,495 | A | * | 6/1995 | Cohn ...................... 250/573 |
| 5,497,008 | A | | 3/1996 | Kumakhov |
| 5,509,297 | A | * | 4/1996 | Miiller et al. ............ 73/54.32 |
| 5,511,416 | A | * | 4/1996 | Shambayati ............ 73/204.21 |
| 5,517,427 | A | * | 5/1996 | Joyce ....................... 702/50 |
| 5,521,698 | A | | 5/1996 | Carroll et al. |
| 5,537,336 | A | * | 7/1996 | Joyce ....................... 702/108 |

(List continued on next page.)

OTHER PUBLICATIONS

Wilson, Bary W, et al, "Modular System for Multi–Parameter In–Line Machine Fluid Analysis" Technology Showcase 2000, JOAP International Condition Monitoring Conference, Apr. 3–6, 2000, Mobile, AL, 78–85.
Goodyear: MEMS Based Smart Tires, IDA 1999.

Primary Examiner—Daniel S. Larkin
Assistant Examiner—Jay L Politzer
(74) Attorney, Agent, or Firm—Woodard, Emhardt, Naughton, Moriarty & McNett

(57) ABSTRACT

The present invention is an apparatus and method for analyzing a fluid used in a machine or in an industrial process line. The apparatus has at least one meter placed proximate the machine or process line and in contact with the machine or process fluid for measuring at least one parameter related to the fluid. The at least one parameter is a standard laboratory analysis parameter. The at least one meter includes but is not limited to viscometer, element meter, optical meter, particulate meter, and combinations thereof.

41 Claims, 7 Drawing Sheets

U.S. PATENT DOCUMENTS

| | | | |
|---|---|---|---|
| 5,569,842 A | | 10/1996 | Silvestri |
| 5,576,498 A | * | 11/1996 | Shambayati ............. 73/861.52 |
| 5,598,451 A | | 1/1997 | Ohno et al. |
| 5,604,441 A | * | 2/1997 | Freese et al. ................ 324/663 |
| 5,657,363 A | | 8/1997 | Hossain et al. |
| 5,712,891 A | | 1/1998 | Benony et al. |
| 5,721,759 A | | 2/1998 | Raatikainen |
| 5,739,916 A | * | 4/1998 | Englehaupt ................. 356/414 |
| 5,742,660 A | | 4/1998 | Majewski et al. |
| 5,790,246 A | | 8/1998 | Kuhnell et al. |
| 5,817,928 A | | 10/1998 | Garvey, III et al. |
| 5,818,578 A | * | 10/1998 | Inman et al. ................ 356/246 |
| 5,982,847 A | * | 11/1999 | Nelson ........................ 378/47 |
| 6,006,154 A | | 12/1999 | Wang |
| 6,009,760 A | | 1/2000 | Jakkula et al. |
| 6,012,325 A | | 1/2000 | Ma |
| 6,031,565 A | | 2/2000 | Getty et al. |
| 6,037,592 A | * | 3/2000 | Sunshine et al. ............ 250/343 |
| 6,043,505 A | * | 3/2000 | Ames et al. ................. 250/577 |
| 6,151,108 A | * | 11/2000 | Kwon et al. .................. 356/70 |
| 6,196,058 B1 | * | 3/2001 | Chen ......................... 73/54.04 |
| 6,226,347 B1 | | 5/2001 | Golenhofen |
| 6,285,734 B1 | | 9/2001 | von Alfthan |
| 6,304,176 B1 | | 10/2001 | Discenzo |
| 6,356,205 B1 | | 3/2002 | Salvo et al. |
| 6,408,048 B2 | | 6/2002 | Opsal et al. |

* cited by examiner

APPARATUS AND METHOD FOR FLUID ANALYSIS

CROSS REFERENCES TO RELATED APPLICATIONS

This application is a continuation-in-part of application Ser. No. 09/447,036 filed Nov. 19, 1999.

STATEMENT REGARDING FEDERALLY SPONSORED RESEARCH OR DEVELOPMENT

This invention was made with Government support under Contract DEAC0676RL01830 awarded by the U.S. Department of Energy. The Government has certain rights in the invention.

FIELD OF THE INVENTION

The present invention relates to an apparatus and method for fluid analysis. Particular embodiments of the present invention relate to on-board analysis of multiple attributes of operating machine fluids necessary for the determination of machine health.

BACKGROUND OF THE INVENTION

It is well known that chemical and physical analysis of a machine fluid can provide information about the condition of the fluid as well as the wear status of the machine in which the fluid is used. Machine fluid analysis is widely used for determination of lubricant condition, lubricant contamination and wear status in engines, drive components and hydraulic systems in fleet or industrial service. For example, lubrication oil analysis is widely used for railroad engines and is conducted by the military on most motorized equipment including aircraft and naval engines and lubricated drive components. In industry, commercial fluid analysis providers offer fluid analysis service for engine and drive train lubricants as well as hydraulic fluids.

Locomotive engine manufacturers such as General Electric (GE) and General Motors Electro-Motive Division (EMD) promulgate recommended limits for wear elements as determined by spectrographic analysis of lubrication oil samples. Manufacturers and railroad operators also set limits on such parameters as water or fuel dilution of lubricating oil, soot and pentane insolubles (compounds in oil that do not dissolve in pentane). These limits indicate when maintenance is required to prevent impending component failures that may result in severe and expensive engine damage. Properly interpreted, the analytical data can also indicate specific maintenance operations that need to be performed on the engine.

Traditionally, an oil sample has been taken from the lubricant reservoir on the engine being analyzed, and each of these parameters was then measured in the laboratory by different instruments for different purposes. Viscosity is measured with a viscometer and provides an indication of possible dilution of the oil by fuel or water. Viscosity can also indicate oil degradation from heat or oxidation. Chemical degradation of the oil (e.g., oxidation, nitration) is commonly determined by infrared (IR) spectrometric analysis, which may also be used to infer total acid number (TAN) and total base number (TBN) for the oil. Water in the oil may also be detected by IR analysis. Slow coolant leaks into the lubricating oil system may be detected by quantitative analysis of boron, chromium or other elements present in the coolant water as salts. Elemental analysis is typically accomplished by atomic emission spectrometry (AES) or other atomic spectroscopy methods, but may also be accomplished by X-ray fluorescence (XRF). Such analyses provide an indication of component wear according to the type and amount of metal(s) in the sample.

Monitoring of machine fluids to specifically determine the parameters described above presently requires that samples of the machine fluid(s) be obtained and sent to a laboratory for chemical and physical analysis. However, the machines for which laboratory analysis is most valuable are often mobile, and may at any time be in remote locations, making sampling and laboratory analysis impractical on a frequent or regular basis. Moreover, the small sample amounts obtained for analysis may not be representative of the bulk machine fluid, and analyses in the laboratory require a day or more to perform. The logistical impracticality of laboratory analysis is overcome in practice with scheduled maintenance and service for machines. Such routine maintenance schedules are designed so that machine fluid change-out occurs prior to the time damage to the machine may result, and are scheduled to ensure that they provide sufficient leeway before a problem is projected to occur. It is believed that the frequency of maintenance and service could be reduced by the use of more frequent and regular machine fluid analysis.

Additionally, there are environments wherein immediate indicators of machine health are critical. As an example, when an engine on a helicopter or airplane fails, the result to passengers can be disastrous. An indication to the pilot of a failing engine, prior to actual engine failure, may provide sufficient time to either save the engine from destruction, or provide time for the pilot to safely return to the ground under power.

On-board or in situ machine fluid analysis has been investigated with several proposed approaches. For example, Voelker et al (U.S. Pat. No. 5,789,665) described a method and apparatus for determining deterioration of lubricating oils by measuring electrical properties of a polymeric matrix or by exploiting volumetric change behavior of the polymeric matrix in the form of beads. Disadvantages of this approach include that it responds only to a single parameter (free water) but does not quantify the free water, and there is a need to replace used polymer beads.

Freese et al. (U.S. Pat. No. 5,604,441) relies on measurement of changes in dielectric properties of a lubricant (oil) in a changing magnetic field. The change in dielectric properties indicates a change in oil condition. Dielectric constant is non-specific and at best may provide an indirect indication of oil degradation. The magnetic field is also used to attract and quantify ferromagnetic particles.

Finally, Boyle et al. (U.S. Pat. No. 5,964,318) designed a system to measure the level and quantity of lubricant in an engine lubricant reservoir. On-board in situ sensors are provided to measure the quantity of lubricant in the system, as well as the quality (temperature, pressure, dielectric and/or viscosity). If the quality drops below a predetermined level, the system diverts a portion of the lubricant to a reservoir for storage or reintroduction as a fuel additive, and a coincident addition of fresh lubricant to the system to maintain the desired level of lubricant. However, the apparatus/process disclosed in the '318 patent is a totally self-contained system; it does not provide an indication to those remotely monitoring engine health of the current status of lubricant within the engine—it is solely an internally-monitored lubricant quality indicator.

The above-cited patents describe measurements that do not provide to remote observers information sufficient to determine the wear status of the machine containing the measured fluid, and so they cannot be used in lieu of standard laboratory oil analysis. In particular, the above-cited patents do not describe a system that allow real time and remote assessment of machine condition, because they lack the capability to determine wear metal concentrations.

On-board measurement and analysis of operational parameters, including determination of fluid levels and fluid and gas temperatures and pressures for a gas turbine engine, has been described (Greitzer et al, 1994). These authors described the use of sensors and artificial neural network software to analyze engine operational status and condition. This approach has been termed machine health monitoring. However, these authors did not attempt to measure standard laboratory analysis parameters for any machine fluid.

Hence, there remains a need for in situ or on-board analysis of machine fluid that provides information similar in nature and utility to that obtained from standard laboratory machine fluid analysis.

BRIEF SUMMARY OF THE INVENTION

The present invention is an apparatus and method for analyzing a fluid used in a machine or in an industrial process line. In one embodiment of the present invention, the apparatus has at least one meter (or sensor) placed proximate a machine and in contact with the machine fluid for measuring at least one parameter related to the machine fluid. The at least one parameter is a standard laboratory analysis parameter. The at least one meter includes, but is not limited to, viscometer, element meter, optical meter, particulate meter, and combinations thereof. Additionally, the results of this machine fluid analysis are made immediately available to remote observers of machine-related system health, whether the analyzed machine fluid is engine lubricant, hydraulic fluid, fuel, coolant fluid, or the like.

As used herein, "proximate" means on or near.

As used herein, "meter . . . in contact with the machine fluid" means that the machine fluid passes to the meter(s) or sensor(s) under pressure of the machine. This is in contrast to collecting a sample in a separate container and introducing the sample to the meter(s) independently of, or separate and distinct from, the machine and the machine pressure.

As used herein, the term or phrase "standard laboratory analysis parameter(s)" refers to parameters specified for direct determination of fluid or machine condition. More specifically, standard laboratory analysis parameter includes, but is in no way limited to, viscosity, low viscosity and high viscosity; pentane insolubles; soot, additive package (presence of chemical additives used to improve lubrication characteristics), oxidation or oil polymer breakdown products, nitration, sulfation, fuel dilution, water concentration; or concentration of specific elements including, but not limited to, iron, lead, copper, silicon, chromium, aluminum, silver, and zinc. In contrast, a non-standard parameter would be an indirect measure including, but not limited to, dielectric constant, polymer swelling, and combinations thereof and are specifically excluded from "standard laboratory analysis parameter".

As used herein, "machine fluid" means any fluid used in the process of operation of machinery. Examples include, but are not limited to, oil, engine oil, differential oil, transmission fluid, hydraulic fluid including, but not limited to, power steering fluid, brake fluid, and hydraulic cylinder fluid, and combinations thereof whether petroleum-based or synthetic; electrical fluid including, but not limited to, battery fluid, condenser fluid (e.g. PCB), and electrochemical electrolyte; refrigerant; cutting fluid; fuel; coolants including water; and combinations thereof.

As used herein, the phrase "remote observer of machine health" means another machine or an individual outside the monitored engine or machine itself, which is programmed or trained to recognize non-routine measurements transmitted by the meter in contact with the machine fluid. The remote observer may be a machine programmed to issue a warning signal if a significantly non-routine measurement is transmitted, or it may be a person, such as the machine operator.

An advantage of the present invention is that it provides to a remote observer of machine health an accurate on-board determination of machine fluid and/or machine condition because of the use of the standard laboratory analysis parameter. Further advantages include real-time machine fluid data capture and machine fluid data capture for remote locations of the machine.

In a preferred embodiment of the present invention, a plurality of standard laboratory analysis parameters is measured or obtained thereby permitting real-time and/or remote assessment of machine and/or machine fluid condition while the machine is in or available for service. An advantage of this preferred embodiment is more timely and cost effective service based on machine condition rather than more traditional service and maintenance based simply on the length of time a machine has been operating.

It is an object of the present invention to provide an apparatus on a machine and in contact with a machine fluid for analysis of the machine fluid by measuring at least one standard laboratory analysis parameter.

It is a still further object of the present invention to provide a system for determining on-board real time parameters of machine fluid systems relating to the health of a machine whereby a plurality of sensors are placed proximate the machine such that a plurality of standard laboratory analysis procedures are determined on-board the machine, with such characteristics being transmitted to a remote observer of machine health.

While an embodiment of the present invention is disclosed with particular reference to an engine lubricant system, it is equally applicable to numerous other systems that determine machine health as well as to industrial fluid processes that would benefit from the types of in situ fluid analysis disclosed herein. Likewise, the invention is not limited to particular apparatuses and methods disclosed herein, but is rather broad enough to encompass the entire system regardless of the particular apparatus utilized.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DETAILED DESCRIPTION OF THE INVENTION

Figure 1:
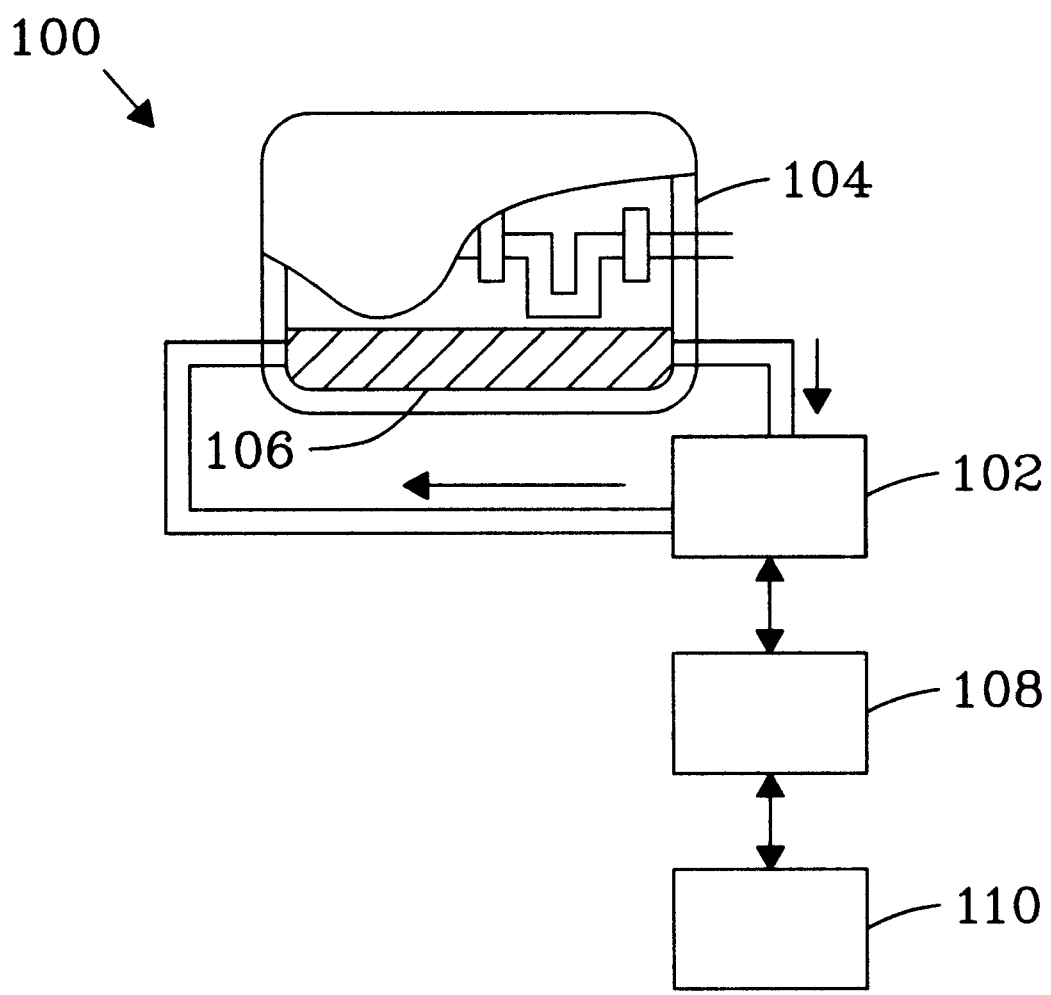
FIG. 1 is a schematic diagram of a single meter embodiment of the present invention.

The present invention is an improvement to an apparatus and method for analyzing a fluid used in, or associated with, a machine or industrial process, wherein the machine is generally, but not necessarily, an engine. In FIG. 1, the apparatus 100 has at least one meter 102 placed proximate the machine 104 (or an industrial process line) and in contact with the machine fluid 106 (or process fluid) for measuring at least one parameter of a standard laboratory analysis parameter related to the machine fluid 106 (or process fluid). The at least one meter includes, but is not limited to, a viscometer, element meter, optical meter, particulate meter, and combinations thereof.

"Meter placed proximate the machine" is herein defined as the meter being either mounted directly on the operating machine, or mounted near the machine(s), rather than in a laboratory separate and remote from the machine(s).

"Machine" 104 is defined as an assembly of mechanical elements wherein at least one of the mechanical elements is in contact with the machine fluid 106 for at least one purpose including, but not limited to, lubrication, heat transfer, electrical charge isolation, electrical charge transfer, movement of another mechanical element and combinations thereof. Without intending to be limited by the following list, machine 104 can include an engine, turbine, transmission, differential, power steering, pump, air compressor, heat pump, refrigerator, machine tool, for example, lathe, milling machine, and saw, electrical motors and associated drive components, and other electrical elements including, but not limited to, batteries, and condensers.

"Vehicle" is defined as an assembly of machines including, but not limited to, railroad locomotives, railroad freight cars (especially refrigerated railroad cars), flatroad vehicles including, but not limited to, automobiles, trucks, motorcycles, and recreational vehicles, off-road vehicles including, but not limited to, tractors, earth movers (e.g. bulldozers, road graders, power shovels, backhoes), cranes, aquatic vehicles including, but not limited to, ships, boats, submarines, and hydrofoils, aircraft including fixed wing propeller, jet, or turboprop, and rotating wing (helicopter), and spacecraft.

Examples of standard laboratory analysis parameters for machine fluids are shown in Table 1. Also shown are the meters that are used to determine these standard laboratory analysis parameters, both measured and derived, in accordance with the present invention. The standard laboratory analysis parameters for oil include, but are not limited to, viscosity; turbidity; particulate size and quantity; total acid number (TAN); total base number (TBN); water content (includes free water and dissolved water); concentrations of cooling water elements including, but not limited to, boron, magnesium, iodine and combinations thereof, wear metal including, but not limited to, iron, lead, copper, silicon, chromium, aluminum, silver, magnesium, tin, and zinc, and combinations thereof.

Standard laboratory analysis parameters for cooling water include, but are not limited to, concentration of carbon, oil presence, fuel presence, concentrations of inhibitors including, but not limited to, chromate and boron, concentrations of rust metals and rust oxides including, but not limited to, iron and iron oxides, and combinations thereof.

The meter 102 for providing these standard laboratory analysis parameters includes, but is not limited to, a viscometer (for viscosity), an energy dispersive X-ray fluorescence (EDXRF) spectrometer utilizing isotopic or X-ray tube X-ray sources (for elemental analysis), non-dispersive IR/visible light meter (for oxidation, nitration, turbidity), and electric or electromagnetic debris/particulate detectors including inductive reactance particle (IRP) and light extinction particle (LEP) counters.

When a combination of meters 102 is used to obtain a combination of standard laboratory analysis parameters, both status or condition of the machine fluid 106 and the machine 104 may be determined in accordance with accepted standards. More

TABLE 1

| Standard Laboratory Analysis Parameter | Meter | Absorption Peak (Wave Number Band, cm$^{-1}$) |
|---|---|---|
| Concentration of wear or additive metals including: Cu, Fe, Cr, Pb, Sn, Ti, Co, Mo, Ni, V, Zn | EDXRF | N/A |
| Viscosity (Kinematic Viscosity) | Viscometer | N/A |
| Fuel Dilution (most hydrocarbon fuels) | Viscometer | N/A |
| Water in Crankcase Oils | NDIR | 3500 to 3150 |
| Water in Esters | | 3700 to 3595 |
| Water in EP Oils | | 3400 to 3250 |
| Soot Loading | | 2000 |
| Oxidation by-products | | 1800 to 1670 |
| Nitration by-products | | 1650 to 1600 |
| Sulfate by-products | | 1180 to 1120 |
| Ester Breakdown I | | 3595 to 3500 |
| Ester Breakdown II | | 3330 to 3150 |
| Phosphate Antiwear (TCP, ZDDP) | | 1025 to 960 |
| Gasoline Dilution | | 755 to 745 |
| Diesel/JP-5/JP-8 Dilution | | 815 to 805 |
| Ethylene Glycol Contamination | | 1100 to 1030 |
| Metal Particles > ~100 μm | IRP Counter | N/A |
| All Particles ~5–100 μm | LEP Counter | N/A |
| Derived Measurements | | |
| Total Acid Number | NDIR | N/A |
| Total Base Number | NDIR | N/A |
| Additive Concentrations | NDIR | N/A | specifically, viscosity provides an indication of possible dilution of the oil by fuel or water. Viscosity can also indicate oil degradation from heat or oxidation. Chemical degradation of the oil (oxidation, nitration, etc.) is commonly determined by IR spectrometric analysis, which may also be used to infer TAN and TBN for the oil. Water in the oil may also be detected by IR analysis. Slow coolant leaks into the lubricating oil system may be detected by EDXRF analysis of boron, chromium or other elements such as iodine or strontium added to the coolant water as salts.

Further advantages are realized by the use of a system controller 108 for controlling the meter(s) 102 and collecting data therefrom. A two-way communicator 110 may also be used to make on-board in situ information available to a remote observer of machine health.

In one embodiment of the present invention, the machine fluid 106 is crankcase oil whereby its condition and the machine 104 (engine) wear on diesel engines of railroad locomotives are monitored by a combination of meters 102. Meters 102 for crankcase oil, as well as for other machine fluids and industrial process fluids, are described in more detail below.

Viscometer

The viscometer provides a measure of viscosity, specifically kinematic viscosity (the terms viscosity and kinematic viscosity are interchangeable herein), at a controlled fluid temperature from (a) the pressure drop across a tube of precise length and inside diameter and (b) the flow rate maintained by a pump and a pressure regulator. The flow rate is maintained at Reynolds number less than 1000, thereby ensuring laminar fluid flow through the tube. The viscosity is determined from classical expressions for laminar fluid flow.

Figure 2:
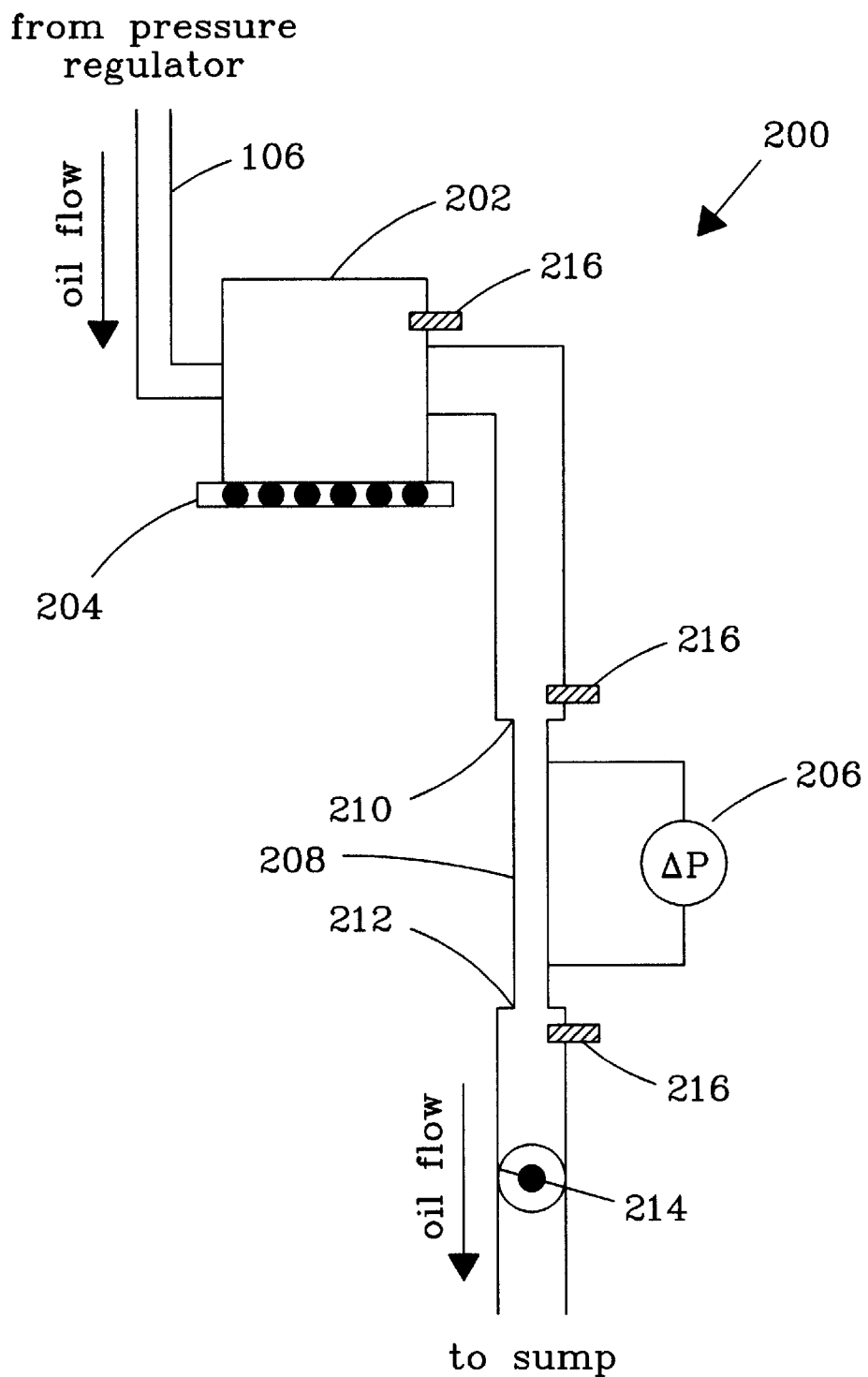
FIG. 2 is a schematic of a viscometer according to the present invention.

Referring to FIG. 2, the viscometer 200 is comprised of several components including, but not limited to: (1) an initial reservoir 202 with a heater 204 (preferably electric resistance heater) that receives the machine fluid 106 at a regulated pressure to control flow through the viscometer 200 and where the machine fluid temperature is adjusted (by heating) to a temperature suitable for measurement, (2) a differential pressure transducer 206 which measures the difference in pressure of the machine fluid 106 flowing through (3) a tube 208 of precise length from the inlet 210 to the outlet 212 of the tube 208, (4) a fluid flowmeter 214 downstream of the tube 208 which measures a constant fluid flow rate through the tube 208, and, (5) one or more thermocouples 216 for measurement of machine fluid temperature through the viscometer. The tube 208 is preferably of a length of about 40 cm, an inside radius of about 0.735 mm, and an outside diameter of about 0.3 cm. The flowmeter 214 may be any flowmeter, but is preferably a model FT0-1NYBBLHC-1 (turbine) with a model LN-5-CMAA-7 (signal conditioner) available from Flow Technologies (Phoenix, Ariz.). Highly accurate measurement of flow cannot be performed over a wide dynamic range due to the changing nature of the flow. The above flowmeter is most accurate near its mid-range and should be operated there. The differential pressure transducer can be of any manufacture as long as the pressure span is sufficient and it possesses an absolute uncertainty of less than 1% over its dynamic range.

Because viscosity is a strong function of temperature, the temperature of the machine fluid must be accurately known to obtain reliable viscosity measurements. For machines that reject heat, it is preferred to measure viscosity at a stable temperature, preferably held slightly above the normal fluid temperature. Heating a machine fluid sample to a temperature slightly above the machine operating temperature is simpler and easier to control than cooling to maintain a lower temperature. The viscometer is preferably insulated to improve temperature stability and control, and preferably temperature controlled with a heater. "Stable temperature" means a temperature that is constant to within about 10° C. of the machine operating temperature, preferably within about 5° C. "Slightly above the machine operating temperature" means a temperature that is from about 0° C. to about 100° C. above the machine fluid temperature, preferably from about 5° C. to about 25° C. above the machine fluid temperature.

A standard viscometer permits viscosity measurement over a typical dynamic range from about 5 cST to 500 cST with an absolute uncertainty of about ±3% over this range. Because variation of viscosity of a machine fluid is much less than the range of a standard viscometer, the uncertainty of a standard viscometer is large enough to mask a change in fluid viscosity. Use of a limited-range viscometer according to the present invention reduces the range to from about 10 cST to about 20 cST, preferably from about 12 cST to about 14 cST with an absolute uncertainty of about ±0.5% over this range, thereby permitting more accurate measure of changes in viscosity of the machine fluid. Although the relative uncertainty is the same between standard and limited-range viscometers, the absolute uncertainty is less for this limited-range viscometer.

For many machine fluid analysis applications, commercially-available miniature electromagnetic viscometers can be used. Such viscometers typically have an absolute uncertainty of about ±1% over a larger limited viscosity range from about 20 cST to about 60 cST.

Element meter

Figure 3:
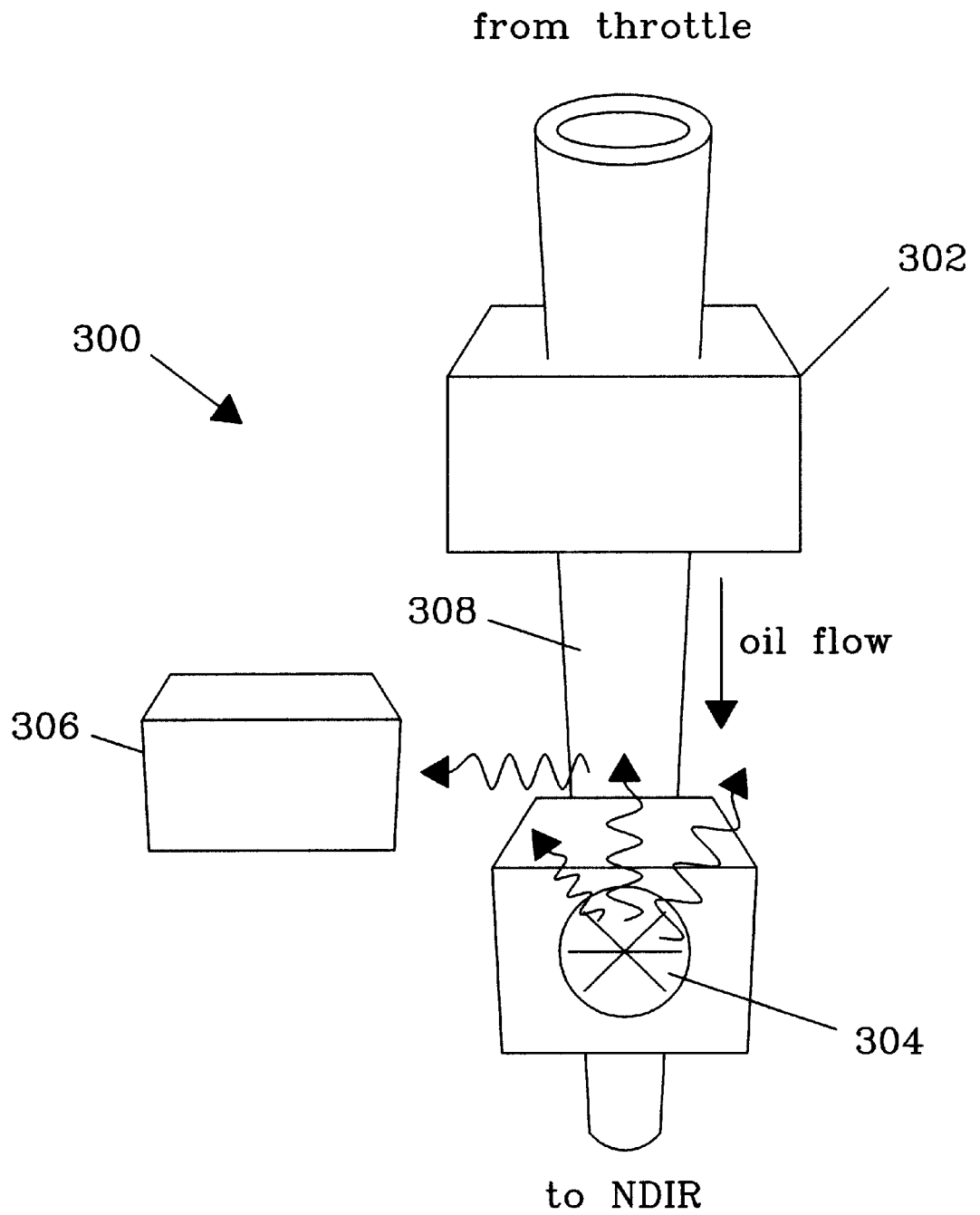
FIG. 3 is a diagram of an energy dispersive X-ray fluorescence spectrometer according to the present invention.

The element meter may be an EDXRF spectrometer utilizing a sealed isotopic X-ray source or source X-rays generated with an X-ray tube, for the purpose of identifying chemical elements, preferably metals in the machine fluid. Referring to FIG. 3, a preferred EDXRF spectrometer 300 receives machine fluid 106 contained in a tube 308, whereby the machine fluid 106 has been cooled in a reservoir 302 so that the machine fluid temperature is below approximately 60° C. An X-ray source 304 in a source block 310 provides X-rays in a suitable energy range (approximately 5–30 KeV) to the machine fluid 106 in the tube 308. The X-ray emitting radionuclides useful as the X-ray source 304 include, but are not limited to, Cadmium-109, Iron-55, Americium-241, and combinations thereof. X-ray tubes are an alternative means to provide X-rays of similar energies.

Any metals in the machine fluid 106 intercept the X-rays and produce an X-ray fluorescence signal. The resulting X-ray fluorescence signal is detected by an X-ray detector 306, preferably a silicon-based detector. The tube 308 exposed to the X-ray source 304 is preferably comprised of low atomic weight elements (e.g., C, H, N) that are relatively transparent to X-rays and do not significantly contribute to the fluorescence background signal in the energy bandwidth of interest. Candidate materials for the tube 308 include polymers, for example, polyimides. The tube 308 must be thin to reduce X-ray attenuation, must withstand any machine vibration, and must be chemically compatible with the machine fluid. For example, the tube 308 used for engine oil analysis in accordance with the present invention was made of polyimide, had a 4.8 mm diameter, and had a 0.08 mm wall thickness.

The absorption of an X-ray by the X-ray detector 306 produces an electronic output pulse with an amplitude proportional to the energy of the absorbed X-ray. Signals from the X-ray detector 306 are amplified and shaped and then the individual pulses from individual X-rays are categorized according to amplitude and recorded with a multichannel analyzer (not shown). A suitable EDXRF spectrometer is model CT 5000 that may be obtained from C-Thru Technologies Corporation (Kennewick, Wash.).

In order to be used commercially, the EDXRF spectrometer must provide shielding and containment of the X-rays from the X-ray source 304 whether the X-rays are generated from an isotopic source or from an X-ray tube. In the present invention, shielding and containment is accomplished by placing the X-ray source 304 in a shielded source block 310 that has been machined and assembled such that there is no path for X-rays to escape the source block 310 except in the unshielded direction toward the tube 308. The X-rays are typically shielded or attenuated by several mm thickness of any high Z block material, but is preferably tungsten because of its lesser weight compared to other high Z materials with equivalent shielding and containment. The inner surface of the source block 310 may be lined with a thin layer of material, such as aluminum or titanium, to reduce the expected EDXRF signal produced from the X-rays interacting with the high Z block material.

Shielding and containment must be such that no radiation or radionuclide material can escape unintentionally, even in the case of a collision or other high-energy impact to the source block 310. At the same time, the source block 310 must allow the machine fluid 106 to pass directly in front of the unshielded X-ray source 304 so that the machine fluid 106 is exposed to X-rays in such a manner to produce an EDXRF signal detectable by the X-ray detector 306.

It is understood that while the primary focus of the description above relates to machine fluids, the present invention should not be so limited. As is apparent to those skilled in the art, such an EDXRF apparatus and method have applications beyond that of machine fluids to any flowing, or intermittently-flowing, fluids. For example, EDXRF elemental analysis would be useful to analyze contaminants, such as suspended metals in a fluid in a process line at an industrial facility.

Non-dispersive optical Meter

Figure 4A:
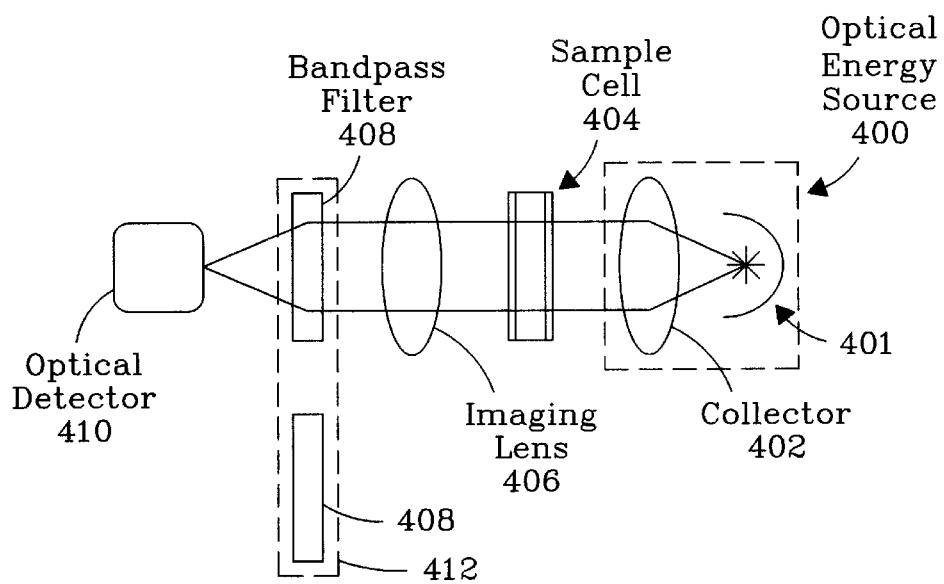
FIG. 4a is a schematic diagram of an optical meter with a tubular sample cell.

The Non-Dispersive (ND) optical meter 420', shown in FIG. 4a, comprises an optical energy source 400 that emits energy in the visible and/or the IR wavelengths, depending on the type of machine fluid degradation that is being measured. The optical energy source 400 may comprise a radiator 401 that is non-coherent including, but not limited to, a filament light source (e.g., where the filament heats the glass envelope which then emits visible and IR radiation) and a blackbody emitter (e.g., where a black material, such as black paint on metal, is heated so that it emits IR radiation) in combination with a collector 402 for guiding non-coherent optical energy through the sample cell 404 containing the machine fluid 106. The geometry of the sample cell 404 may be tubular or planar. Alternatively, the optical energy source 400 may comprise a radiator 401 that is coherent (e.g., quantum cascade laser(s), laser diode(s)) operating at specific visible or IR wavelengths, with or without a collector 402 depending upon divergence of the laser and distance of the radiator 401 from the sample cell 404. In the case of a radiator 401 that is non-coherent, the collector 402 may be a reflector and/or a lens. The transmitted energy is then collected by an imaging lens 406. In the case of a radiator 401 that is coherent, an imaging lens 406 may or may not be needed.

Coherent optical energy is narrow band in terms of optical frequencies, thereby permitting use of an optical detector 410 in the absence of a bandpass filter 408. Multiple optical signals of different optical frequencies of coherent optical energy may be obtained by use of two or more radiators 401 radiating at different optical wavelengths.

Non-coherent optical energy is wide band in terms of optical frequencies. Accordingly, non-coherent optical energy transmitted through the machine fluid is passed through a bandpass filter 408 that transmits only certain specific wavelengths to an optical detector 410. The sample cell 404 may transmit visible, as well as IR, radiation. Materials such as a thin film of polyethelene, zinc selenide, or calcium fluoride, are commercially available that transmit in both the visible and IR wavelength regions of interest. Multiple optical signals of different optical frequencies of non-coherent optical energy may be obtained by using a filter wheel 412 to hold two or more bandpass filters 408 that transmit at specific wavelength bands.

The transmissivity of a sample cell 404 with no machine fluid in it is compared to a sample cell 404 with machine fluid 106 in it. The difference in transmissivity indicates the condition (e.g., degradation) of the machine fluid. The wavelength bands that exhibit a certain type of condition will vary depending on the type of machine fluid examined. Soot and fine particles will be detected by a decrease in the transmissivity of the machine fluid in selected wavelength regions.

Figure 4B:
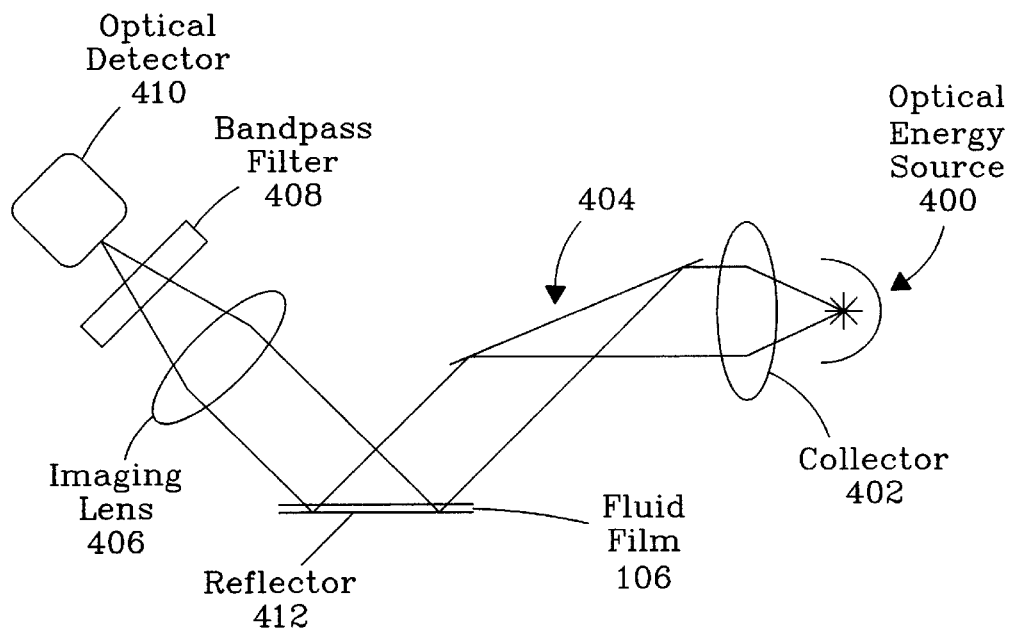
FIG. 4b is a schematic diagram of an optical meter with a planar sample cell.

Another embodiment of the ND optical meter 420", shown in FIG. 4b, comprises a sample cell 404 wherein the sample cell 404 is a mirror system. The principle behind this embodiment is similar to that of FIG. 4a, except now the optical energy is transmitted through a film of the machine fluid 106 twice. In this case, the sample cell 404 includes a reflector 412, which can be either a glass mirror with a front surface reflector or a metal mirror. The optical energy reflected by the reflector 412 is retransmitted through the machine fluid 106, to the imaging lens 406 (for non-coherent optical energy), bandpass filter 408, and optical detector 410.

According to the present invention, this IR meter lacks a dispersive element compared to standard IR meters. Use of a dispersive element requires elimination of all relative motion between the dispersive element and other elements of the standard IR meter which disqualifies its use on a machine subject to vibration. Omitting the dispersive element according to the present invention provides a non-dispersive IR meter that is insensitive to the vibration of a machine.

Particulate meter

Particulate meters used in accordance with the present invention may be one of several types that are commercially available. For detection of ferromagnetic particles, for example, the Vickers Tedeco Smart Zapper™ or Vickers Tedeco IQ™ (Eaton TEDECO Glenolden, Pa.) may be selected. These particle detectors are also known as "debris monitors" or "chip detectors". They attract and retain ferromagnetic particles with a magnet mounted concentric with, and in close proximity to, a conductive ring.

For metallic particles of a size greater than approximately 100 microns, the Metal Scan™ system from GASTOPS (Toronto, Canada) may be used. Metal Scan™ detects the particles by the change in inductive reactance the metal particles induce in a coil system when the particles pass through the coil in the machine fluid stream.

A particulate meter may also be selected from a number of optical particle counters including the laser light extinction particle counting meter available from ART Instruments, Inc. (Grants Pass, Oreg.). The light extinction or light refraction counters have the capability to detect both metallic and non-metallic particles in sizes down to 5 microns or less.

Controller

Figure 5:
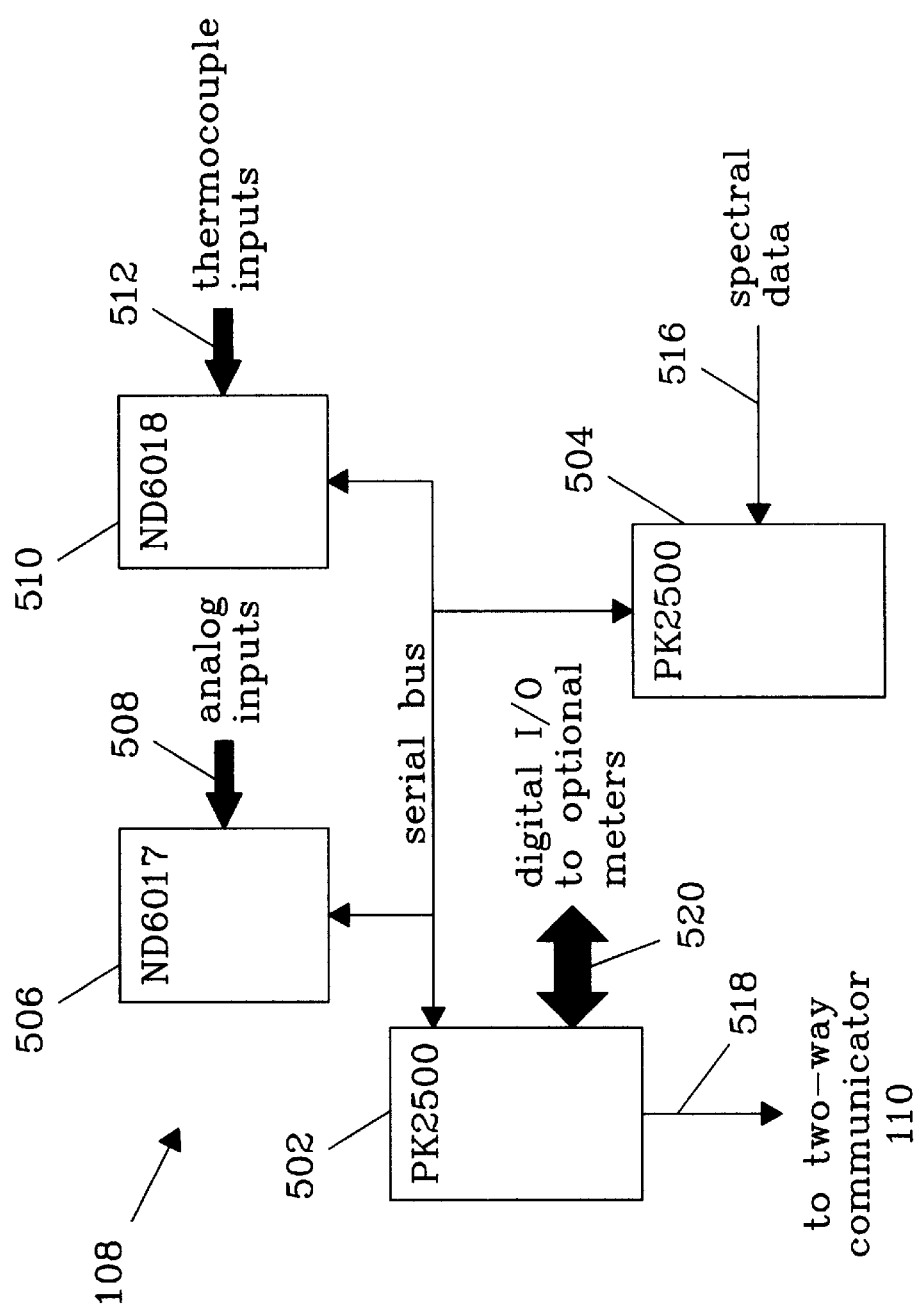
FIG. 5 is a schematic representation of the communicator of the present invention.

In FIG. 5, the system controller 108 implements automated control and data acquisition such that standard laboratory analysis parameters can be determined and recorded without human intervention. Continuous logging of data by the system controller 108 creates a record that can be used to determine trends and predict maintenance schedules. It is preferred that the system controller 108 contain one or more embedded controllers 502 and 504, for example PK2500, available from Z-World (Davis, Calif.), that is c-programmable. It is further preferred that each embedded controller 502 have a microprocessor, memory, digital input/output, analog input, and mass storage (optional) for control of the meter(s), recording of standard analysis parameter(s) and optional operation of a two-way communicator 110. An 8-channel analog-to-digital converter 506, 510, for example ND-6018, available from Circuit Specialists (Mesa, Ariz.), converts analog signals including, but not limited to, 4–20 mA pressure transducer signals 508, thermocouple signals 512, meter signals and combinations thereof.

Preferably, an embedded controller 504 controls and acquires data from meters such as the EDXRF spectrometer 300 which generate spectral data 516, non-dispersive optical meter, viscometer, solid state cooling device, resistive heater (s), particulate meter(s) and combinations thereof. The embedded controller 504 has sufficient memory and, optionally, mass storage to record data over an extended period of time. Another embedded controller 502 communicates to a two-way communicator 110 or, optionally, a laptop computer over serial I/O 518 and provides control and data acquisition for additional optional meters over digital I/O 520. The embedded controller 502 also performs reduction of the data produced by the meters and the resulting standard analysis parameters are stored in memory or, optionally, on mass storage. The embedded controller 502 also has sufficient storage and optional mass storage to record standard analysis parameter(s) over an extended period of time. If standard analysis parameters exceed preset limits, the embedded controller 502 can initiate an emergency call through the two-way communicator 110.

Figure 6:
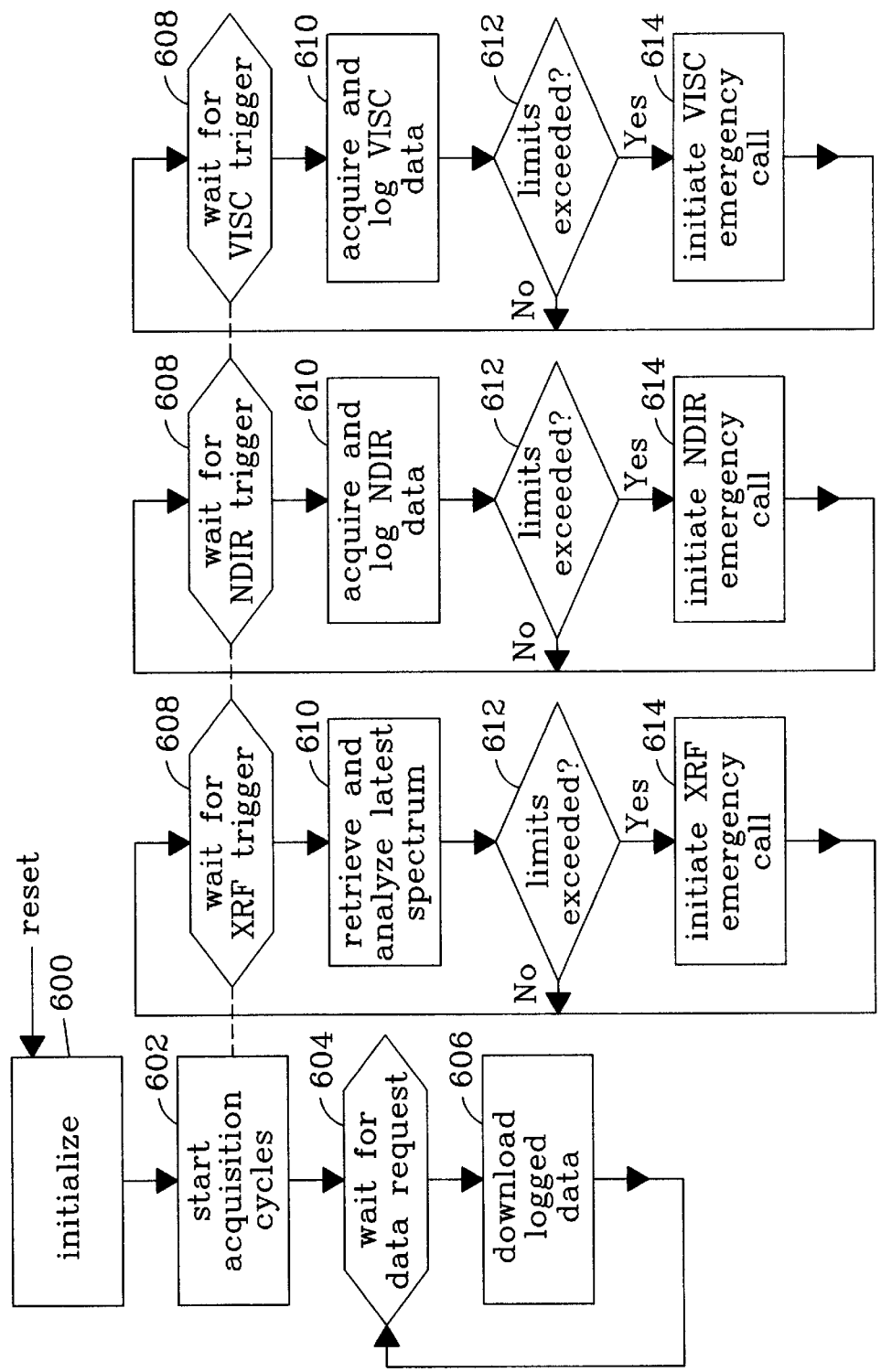
FIG. 6 is a flow chart of software within the controller.

The system controller 108 may be programmed according to the flow chart in FIG. 6. A reset may either be a user-initiated reset such as when the program is first loaded or a recovery-mode reset resulting from a power failure or software or hardware failure. After reset, interfaces are initialized 600 by setting variables to initial values for a user-initiated reset or restored to previous values for recovery-mode resets. The acquisition cycles are then started 602. This initiates a separate process for each meter in the system. The main process then waits for download requests 604. Upon receipt of a download request, the main process transfers logged data 606 to the two-way communicator 110 or optional laptop. All meter processes wait to be triggered 608 either by communications from the meter or by a timer. Data are retrieved from the meter(s) and processed and logged as required 610. A test for data outside flag limits 612 causes an emergency call 614 for meter data outside the flag limits.

Communicator

As shown in FIG. 5, another improvement is a two-way communicator 110 connected to the system controller 108 for receiving interrogation signals and for transmitting data, thereby obtaining an in situ or on-board machine fluid analysis. Two-way communication enables remote monitoring of machine and machine fluid condition. A communicator 110 may be a two-way, cell-phone based, communicator that may be obtained from Highway Master Systems (Muldrow, Okla.).

System

Figure 7:
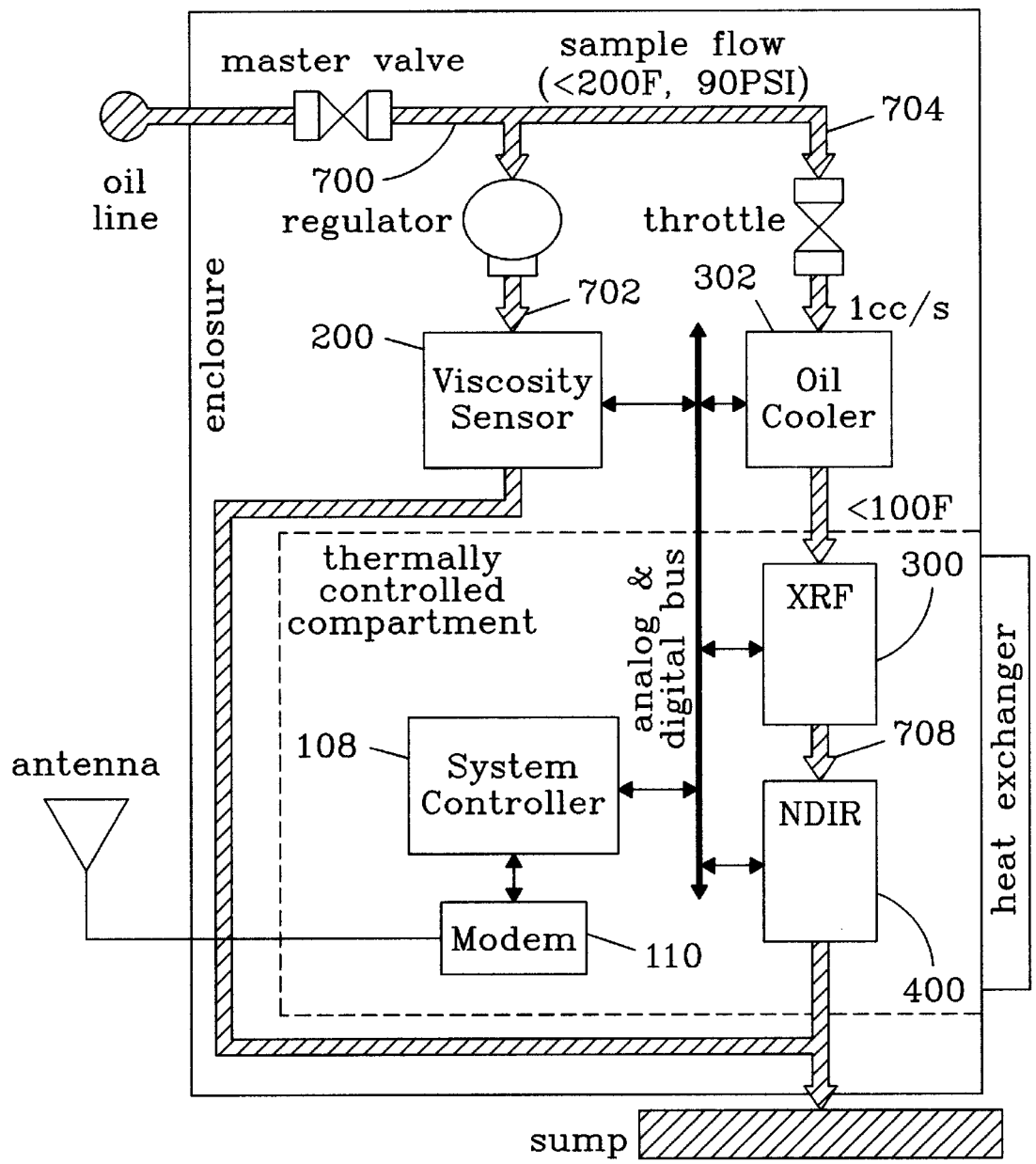
FIG. 7 is a schematic diagram of a multiple meter embodiment of the present invention.

An embodiment of the present invention is a system for machine fluid analysis as shown in FIG. 7. A sample line 700 leads from a pressurized machine fluid line whereby a first branch sample line 702 leads to the viscometer 200, and a second branch sample line 704 leads through a throttle 706 to the reservoir 302 of the EDXRF spectrometer 300. After passing through the EDXRF spectrometer 300, the machine fluid flows through a connecting tube 708 to the ND optical meter 420, preferably an IR meter. Thus, in this embodiment, the machine fluid sample is split such that one part runs through the viscometer 200 while the other part runs through both the EDXRF spectrometer 300 and the ND optical meter 420. Signals from the meter(s) are collected by the system controller 108 and may be transmitted by the communicator 110.

In this embodiment of the present invention, the machine fluid analysis system comprises a microprocessor-controlled power supply (not shown) and system controller 108. The system controller 108 comprises microprocessor controllers for the EDXRF spectrometer 300, ND optical meter 420, viscometer 200, and the laser light extinction particle counter (not shown) and a sample acquisition system (not shown) to adjust the pressure and temperature of the incoming machine fluid, as required. The system can operate in an autonomous mode wherein data are collected from the parameter meters and stored, or it can operate under control of a user interface wherein a human operator directs the functions of the parameter meters.

For deployment on a machine in an environment including, but not limited to, vehicle, industrial plant, outdoors, airborne, outer space, and combinations thereof, the system is preferably housed in an enclosure 710 that is shock mounted to reduce vibration and contains, or is connected to, an electrical power supply. Situated within the enclosure 710 may be a cooler(s) for cooling the X-ray and IR detectors and removing process heat. In another embodiment, the cooler(s) comprises solid state electrical cooling assemblies known as Peltier baffle devices.

CLOSURE

While various embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A machine fluid analysis system comprising:
   at least first and second sensors contacting a machine fluid under pressure of the machine;
   a controller operable to collect data from the sensors for transmission to a remote location; and
   a two-way wireless communicator coupled to the controller for receiving interrogation signals and for transmitting the collected data to the remote location;
   wherein the first sensor includes an X-ray fluorescence meter including an X-ray source providing X-rays in the energy range of 5 KeV to 30 KeV and a thin walled tube of low element weight composition substantially transparent to source X-rays, the tube defining a fluid flow path past the X-ray source, and
   wherein the second sensor includes at least one sensor selected from the group consisting of viscometer, optical meter, and particle counter.

2. The system of claim 1 wherein the second sensor includes a viscometer and wherein machine fluid contacting the X-ray fluorescence meter is at a substantially lower temperature than machine fluid contacting the viscometer.

3. The system of claim 2 wherein the X-ray fluorescence meter and the viscometer are coupled to a machine fluid line in parallel and a machine fluid cooler is upstream and in series with the X-ray fluorescence meter.

4. The system of claim 2 wherein the viscometer is an electromagnetic viscometer.

5. The system of claim 2 wherein the viscometer is a viscometer tube, a differential pressure transducer mounted on opposite ends of the viscometer tube, and a flowmeter in line with the viscometer tube.

6. The system of claim 1 wherein the controller includes at least one microprocessor, and
   wherein the X-ray fluorescence meter includes an X-ray detector for receiving a produced X-ray fluorescence signal, a multi-channel analyzer for counting the number of X-ray photons in specific energy ranges, and a software for quantitative determination of the relative and absolute concentration of elements in the fluid.

7. The system of claim 6 wherein the flow fluid into the fluid flow path of the X-ray fluorescence meter is intermittent.

8. The system of claim 6 wherein the flow of fluid into the fluid flow path of the X-ray fluorescence meter is substantially continuous.

9. The system of claim 1 further comprising a two way communications bus between the controller and each of the plurality sensors.

10. The system of claim 1 wherein the second sensor includes an optical meter including an optical source operable to pass optical energy through the machine fluid and an optical detector operable to receive the optical energy passed through the machine fluid, and wherein there is no optical dispersive element between the optical energy source and the machine fluid or between the machine fluid and the detector.

11. The system of claim 10 wherein machine fluid is passed through a tubular cell in the optical meter.

12. The system of claim 10 wherein machine fluid is passed over a planar cell in the optical meter.

13. The system of claim 10 wherein optical energy source includes a non-coherent radiator and the optical meter includes a bandpass filter for filtering optical energy passed through the machine fluid.

14. The system of claim 10 wherein the optical energy source includes a coherent radiator.

15. The system of claim 3 further comprising an optical meter connected in series with the X-ray fluorescence meter.

16. The system of claim 15 wherein the optical meter and the X-ray fluorescence meter are contained in a thermally controlled compartment and the viscometer is outside the thermally controlled compartment.

17. The system of claim 16 further comprising a particle counter.

18. The system of claim 1 wherein the second sensor includes an optical particle counter operable to detect the presence of metallic or non-metallic particles.

19. A machine fluid analysis system comprising:
a plurality of different sensors contacting a fluid under pressure of a machine, wherein at least two of the plurality of sensors are selected from the group consisting of optical meter, viscometer, element meter, and particle counter;
a controller operable to collect data from the plurality of sensors for transmission to a remote location; and
a two-way wireless communicator coupled to the controller for receiving interrogation signals and for transmitting the collected data to the remote location; and
a fluid cooler operably coupled to at least one of the sensors;
wherein fluid is provided to different ones of the plurality of sensors at substantially different temperatures.

20. The system of claim 19 wherein the plurality of sensors include an element meter operable to determine the concentration of at least one specific element in the fluid.

21. The system of claim 20 wherein the specific element is selected from the group consisting of iron, lead, copper, silicon, chromium, aluminum, silver, and zinc.

22. The system of claim 20 wherein the element meter is an X-ray fluorescence meter including an X-ray source, a thin walled polymeric tube substantially transparent to source X-rays and providing a flow path past the X-ray source, and an X-ray detector for receiving an X-ray fluorescence signal from the fluid in the tube.

23. The system of claim 22 wherein the X-ray fluorescence meter includes an X-ray detector for receiving a produced X-ray fluorescence signal, a multi-channel analyzer for counting the number of X-ray photons in specific energy ranges, and software for quantitative determination of the relative and absolute concentration of elements in the fluid.

24. The system of claim 23 wherein each of the plurality of sensors are operable to determine a different machine fluid parameter selected from the group consisting of viscosity, pentane insolubles, soot, additive package, oxidation, or oil polymer breakdown products, nitration, sulfation, fuel dilution, water concentration, and concentration of a specific element.

25. The system of claim 22 wherein the X-ray fluorescence meter is provided in a thermally controlled compartment and the fluid cooler is provided in series with the X-ray fluorescence meter outside the thermally controlled compartment.

26. The system of claim 25 wherein a viscometer is outside the thermally controlled compartment and fluidly coupled in parallel with the X-ray fluorescence meter.

27. The system of claim 25 wherein the plurality of sensors includes an optical meter including an optical source operable to pass optical energy through the fluid and an optical detector operable to receive the optical energy passed through the fluid, and wherein there is no optical dispersive element between the optical energy source and the fluid or between the fluid and the detector.

28. The system of claim 27 wherein fluid is passed through a tubular cell in the optical meter.

29. The system of claim 27 wherein fluid is passed over a planar cell in the optical meter.

30. The system of claim 27 wherein optical energy source includes a non-coherent radiator and the optical meter includes a bandpass filter for filtering optical energy passed through the fluid.

31. The system of claim 27 wherein the optical energy source includes a coherent radiator.

32. A fluid analysis system comprising:
a plurality of different sensors contacting a fluid under pressure of a machine, wherein each of the plurality of sensors are operable to determine a different machine fluid parameter selected from the group consisting of viscosity, pentane insolubles, soot, additive package, oxidation or oil polymer breakdown products, nitration, sulfation, fuel dilution, water concentration, and concentration of a specific element;
a controller operable to collect data from the plurality of sensors for transmission to a remote location; and p1 a two-way wireless communicator coupled to the controller for receiving interrogation signals and for transmitting the collected data to the remote location; and p1 a thermally controlled compartment wherein at least one of the sensors is inside of and another is outside of the thermally controlled compartment whereby fluid is provided to different ones of the plurality of sensors at substantially different temperatures.

33. The system of claim 32 wherein a viscometer is outside the thermally controlled compartment.

34. The system of claim 32 wherein a non-dispersive optical meter is inside the thermally controlled compartment.

35. The system of claim 32 wherein an X-ray fluorescence meter is inside the thermally controlled compartment.

36. The system of claim 35 wherein the X-ray fluorescence meter includes an X-ray source, a thin walled polymeric tube substantially transparent to source X-rays and providing a flow path past the X-ray source, and an X-ray detector for receiving an X-ray fluorescence signal from the fluid inside the tube.

37. The system of claim 32 wherein the plurality of sensors are selected from the group consisting of viscometer, non-dispersive optical meter, element meter, and particle counter.

38. The system of claim 2 wherein the viscometer has a dynamic range from about 10 cST to about 60 cST with an absolute certainty of no greater than ±1%.

39. The system of claim 26 wherein the viscometer has a dynamic range from about 10 cST to about 60 cST with an absolute certainty of no greater than ±1%.

40. The system of claim 31 wherein the coherent radiator includes a quantum cascade laser.

41. The system of claim 14 wherein the coherent radiator includes a quantum cascade laser.

* * * * *